United States Patent [19]

Miura

[11] Patent Number: 5,046,948

[45] Date of Patent: Sep. 10, 1991

[54] ORTHODONTIC COIL SPRING

[75] Inventor: Fujio Miura, Sakae, Japan

[73] Assignee: GAC International, Inc., Central Islip, N.Y.

[21] Appl. No.: 501,603

[22] Filed: Mar. 29, 1990

[30] Foreign Application Priority Data

May 29, 1989 [JP] Japan .................. 1-60964[U]

[51] Int. Cl.$^5$ .................................. A61C 3/00
[52] U.S. Cl. ................................ 433/21; 433/18; 433/20
[58] Field of Search .................. 433/18, 19, 20, 21

[56] References Cited

U.S. PATENT DOCUMENTS

| 3,235,965 | 2/1966 | Muir | 433/21 |
|---|---|---|---|
| 3,293,747 | 12/1966 | Denholtz | 433/21 |
| 3,374,542 | 3/1968 | Moylan, Jr. | 433/20 |
| 3,593,421 | 7/1971 | Brader | 433/21 |
| 3,618,214 | 11/1971 | Armstrong | 433/19 |
| 3,815,237 | 6/1974 | Wallshein | 433/21 |
| 4,037,324 | 7/1977 | Andreasen | 32/14 A |
| 4,315,739 | 2/1982 | Cain | 433/21 |
| 4,490,112 | 12/1984 | Tanaka et al. | 433/20 |
| 4,849,032 | 7/1989 | Kawaguchi | 148/11.5 R |

FOREIGN PATENT DOCUMENTS 57-171653 10/1982 Japan .

OTHER PUBLICATIONS

20 Kirk-Othmer, Encyclopedia of Chemical Technology, 726, 733 (3d ed. 1982), New York.
Miura et al., "The Super-Elastic Japanese NiTi Alloy Wire for use in Orthodontics," American J. of Orthodontics and Dentofacial Orthopedics, vol. 94, No. 2, Aug. 1988, pp. 89-96.
Abstract of "Studies on the Super-Elastic Japanese NiTi Alloy Coil Springs" in the Program for the 34th Annual Meeting of the Japanese Association for Dental Research, held Dec. 4 and 5, 1986.
Abstract of "Studies on Mechanical Properties of New Superelastic NiTi Wire," from the 41st Annual Session of the Japan Orthodontic Society, held Sep. 17-19th, 1982.
"The Super-Elastic Property of the Japanese NITI Alloy Wire for use in Orthodontics," Am. J. Orthod. and Dentofacial Orthopedics, Miura et al., vol. 90, No. 1, pp. 1-10 (Jul. 1986).
"Characteristics of Deformation and Transformation Pseudoelasticity in Ti-Ni Allous," Miyazaki et al., Journal De Physique, vol. C4, No. 12, pp. C4-255-260, Dec. 1982.
"Transformation Pseudoelasticity and Deformation Behavior in A Ti-50.6 at % Ni Alloy," Miyazaki et al., Scripta Metallurgica, vol. 15, pp. 287-292.
Literature from Associated Spring, Barnes Group Inc., pp. 13 and 15.

Primary Examiner—Gene Mancene
Assistant Examiner—Michael Lynch
Attorney, Agent, or Firm—Kenyon & Kenyon

[57] ABSTRACT

A continuous-length orthodontic coil spring is made from a shape-memory alloy wire wound into a coil. The coil defines a plurality of open coil sections defining spaces between the turns thereof, and closed coil sections formed between the open coil sections. The closed coil sections are tightly wound with insubstantial spacing between the turns thereof. The coil spring is made of a Ni-Ti alloy wire, and is heat treated to impart a predetermined range of spring force within a superelastic zone of deflection. The continuous-length coil spring is cut through the closed coil sections to form several shorter-length coil springs therefrom. The closed coil sections on either end of the shorter-length coil springs are thus adapted to engage the orthodontic brackets mounted to a patient's teeth, to accurately impart the force of the spring to the brackets.

19 Claims, 2 Drawing Sheets

PRIOR ART

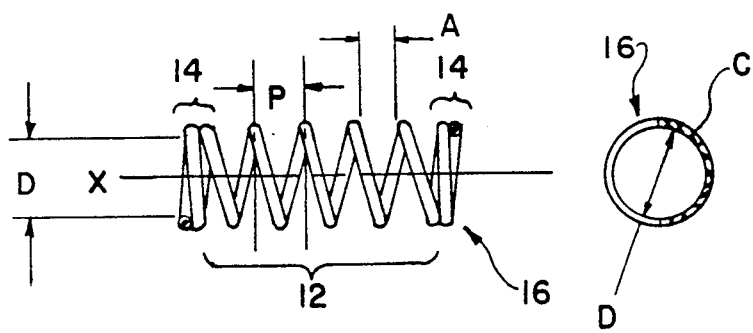
FIGURE 3
FIGURE 4
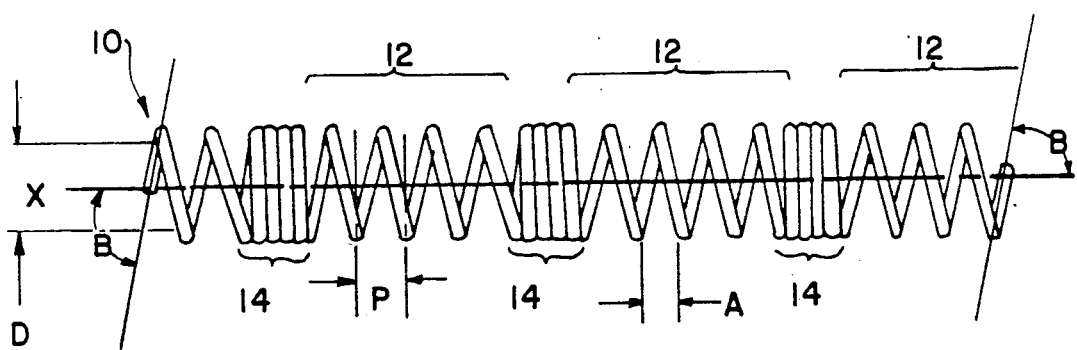
FIGURE 5

ORTHODONTIC COIL SPRING

FIELD OF THE INVENTION

The present invention relates to coil springs and, in particular, to orthodontic coil springs made of alloy wires exhibiting shape-memory properties.

BACKGROUND INFORMATION

An orthodontic coil spring made of an alloy wire exhibiting shape memory properties, such as nickel-titanium (Ni-Ti) alloy wire, is shown in U.S. Pat. No. 4,849,032. The Ni-Ti alloy wires exhibiting shape-memory properties are often referred to as "shape-memory alloy wires." Shape-memory alloy wires frequently exhibit excellent superelastic and spring-back properties.

Superelasticity occurs when the stress value remains substantially constant up to a certain point of wire deformation, and when the wire deformation is reduced, the stress value again remains substantially constant. Therefore, a coil spring made of a shape-memory alloy wire can maintain a substantially constant load value throughout a zone of deflection. Because shape-memory alloy wires possess excellent spring-back properties, they can also be deflected to greater degrees than other types of wires, without causing permanent deformation of the wire.

A shape-memory coil spring is made by winding a shape-memory alloy wire, such as a Ni-Ti alloy wire, into a coil. If the coil spring is to be used as an open or compression coil spring, then it is wound into a coil defining spaces between each turn thereof. If the coil spring is to be used as a closed or tension coil spring, then it is tightly wound into a close contact shape substantially without any spacing between its turns. Tension coil springs are provided with hooked portions on their ends to connect the springs to orthodontic appliances.

In FIG. 1, a typical open shape-memory alloy coil spring is indicated by the reference numeral 1. The coil spring 1 is fitted over an archwire 2 and mounted between two orthodontic brackets 3. The orthodontic brackets 3 are in turn mounted to adjacent teeth T1 and T2. The coil spring 1 is an open or compression coil spring, and is thus wound with spacing between its turns. As indicated by the arrow shown in FIG. 1, the coil spring 1 is used to shift the tooth T1 away from the tooth T2, and thus into the space between the teeth T1 and T3.

One advantage of the coil spring 1 is that because it is made of a shape-memory alloy wire, it exerts a substantially constant spring force throughout a zone of deflection, often referred to as the "superelastic zone of deflection." Therefore, if the distance that the tooth T1 is to be shifted is within the superelastic zone of deflection of the spring 1, the spring 1 can be used to apply a substantially constant spring force throughout the entire movement of the tooth.

An open shape-memory alloy coil spring, like the coil spring 1, is typically made by winding a shape-memory alloy wire into a continuous-length open coil spring. The continuous-length coil spring is wound to define substantially constant spacing between the turns thereof. The continuous-length coil spring is heat treated, and is then cut into a number of shorter-length coil springs. The length of each shorter coil spring is dimensioned so that the spring will be compressed when fitted over an archwire in the space provided between the orthodontic brackets mounted on a patient's teeth.

One problem with open shape-memory alloy coil springs, is that because they are cut from larger continuous-length coil springs, the ends of each coil spring are not adapted to properly engage the orthodontic brackets mounted to a patient's teeth. Usually, the ends of each spring are cut at the middle of a turn or, that is, at the midpoint of the space between two turns of the spring. As a result, the free ends of such a coil spring are oriented at oblique angles relative to the longitudinal axis of the spring. Thus, when the spring is mounted over an archwire, only the tips of its free ends engage the orthodontic brackets.

The tips of the spring, however, are not shaped or oriented to conformably engage the surfaces of the brackets. This problem is enhanced with open shape-memory alloy coil springs, because they are typically deflected or opened to a greater degree than other types of orthodontic open coil springs. As a result, the force of an open shape-memory alloy coil spring is usually not applied to the orthodontic brackets in a smooth and reliable manner.

It is an object of the present invention, therefore, to provide an orthodontic coil spring that overcomes the problems of known shape-memory alloy coil springs.

SUMMARY OF THE INVENTION

The present invention is directed to an open orthodontic coil spring for imparting forces to orthodontic appliances mounted to a patient's teeth. The orthodontic coil spring comprises a shape-memory alloy wire exhibiting superelastic properties wound into a coil. The coil includes at least one open coil section between the free ends thereof, which defines predetermined spaces between its turns. The free ends of the coil are tightly wound substantially without any spacing between the turns thereof. The free ends of the coil are thus adapted to substantially engage orthodontic appliances to impart the spring forces thereto.

In one coil spring of the present invention, the shape-memory alloy wire is a Ni-Ti alloy wire, and the coil spring is heat treated to impart a substantially predetermined range of spring force within a superelastic zone of deflection. Preferably, each of the free ends of the coil includes at least 1-½ turns. The coil spring thus defines an engaging surface on either end thereof. The turns defining the engaging surfaces are preferably oriented substantially perpendicular to the longitudinal axis of the coil spring. Each of the engaging surfaces is equal in length to about one-half of a turn of the coil spring.

The present invention is also directed to a continuous-length coil spring for forming several shorter-length open orthodontic coil springs therefrom. The continuous-length coil spring comprises a shape-memory alloy wire exhibiting superelastic properties wound into a coiled shape. The coiled shape includes a plurality of open coil sections defining predetermined spaces between the turns thereof, and closed coil sections formed between the open coil sections. The closed coil sections are tightly wound with insubstantial spacing between the turns thereof. The continuous-length coil spring is separable into more than one coil spring by cutting through the shape-memory alloy wire in at least one of the closed coil sections.

In one coil spring of the present invention, each of the open coil sections includes the same number of turns and each of the closed coil sections includes the same number of turns. Preferably, each open coil section includes about five turns and each closed coil section includes about three turns. The shape-memory alloy wire is preferably made of a Ni-Ti alloy.

The present invention is also directed to a method of making orthodontic coil springs, comprising the following steps:

winding a shape-memory alloy wire exhibiting superelastic properties into a coil defined by a plurality of open coil sections and closed coil sections formed between the open coil sections, wherein the open coil sections define predetermined spaces between the turns thereof, and the closed coil sections are tightly wound with insubstantial spacing between the turns thereof; and cutting through the shape-memory alloy wire in at least one of the closed coil sections to form at least two coil springs therefrom.

In one method of the present invention, each of the open coil sections are formed with the same number of turns and each of the closed coil sections are formed with the same number of turns. The shape-memory alloy wire is preferably made of a Ni-Ti alloy.

One advantage of the present invention, is that because the free ends of the coiled wire are tightly wound with insubstantial spacing between the turns thereof, the coil spring has relatively large, smooth surfaces on either end thereof for engaging orthodontic appliances. As a result, the substantially constant force of the coil spring can be accurately and smoothly imparted to orthodontic appliances. Thus, the problems of known open, shape-memory alloy coil springs, wherein only the tips of the free ends of the coil springs engage the appliances, are overcome by the open coil spring of the present invention.

Other advantages of the apparatus and method of the present invention will become apparent in view of the following detailed description and drawings taken in connection therewith.

BRIEF DESCRIPTION OF THE DRAWINGS

FIG. 3 is a plan view of an open orthodontic coil spring embodying the present invention cut from the continuous-length coil spring of FIG. 2.

FIG. 4 is a side plan view of the coil spring of FIG. 3.

FIG. 5 is a partial plan view of another continuous-length coil spring embodying the present invention.

DETAILED DESCRIPTION

Figure 1:
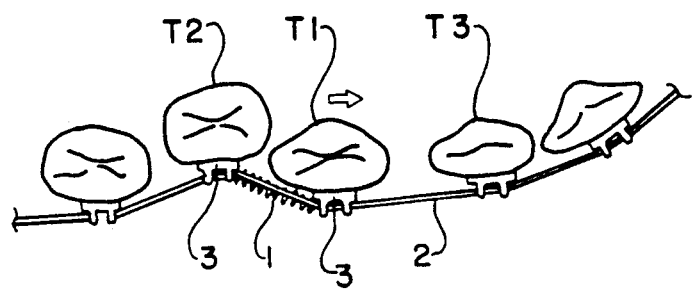
FIG. 1 is a top plan view of a known orthodontic open, shape-memory alloy coil spring mounted between two orthodontic brackets to move a patient's teeth.
Figure 2:
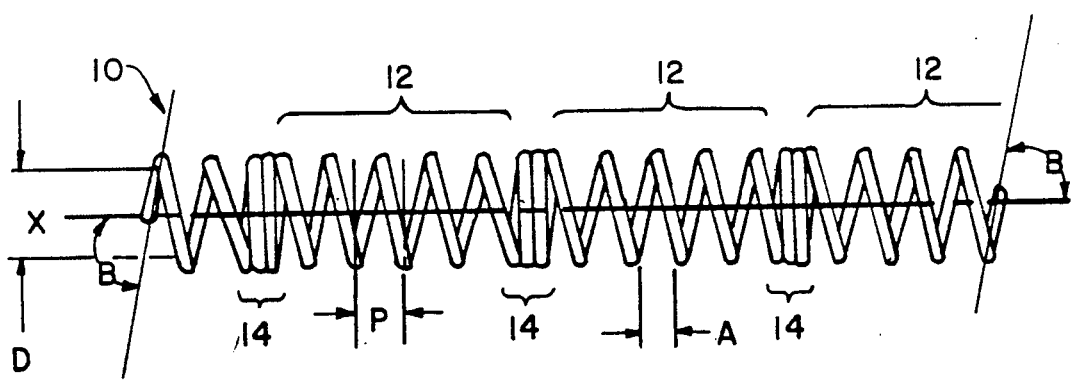
FIG. 2 is a partial plan view of a continuous-length coil spring embodying the present invention.

In FIG. 2, a continuous-length coil spring embodying the present invention is indicated generally by the reference numeral 10. The continuous-length coil spring 10 is made of a shape-memory alloy wire, such as a Ni-Ti alloy wire, which is wound into a coil. When the coil spring 10 is in a relaxed state (neither being stretched nor compressed), it defines a plurality of open coil sections 12 and closed coil sections 14 located therebetween. The open coil sections 12 are wound with a pitch "P", so as to define substantially equal predetermined spaces "A" between the turns thereof. The closed coil sections 14, on the other hand, are tightly wound substantially without any spacing between the turns thereof.

As shown in FIG. 2, each individual turn of the open coil sections 12 is oriented at an oblique angle "B" relative to the longitudinal or helical axis "X" of the coil spring. The turns of the closed coil sections 14, on the other hand, are substantially perpendicular to the X axis. The coil spring 10 is wound so that each open coil section 12 includes about five turns and each closed coil section 14 includes about three turns. As can be seen, the same winding pattern is repeated throughout the length of the coil spring 10. After the coil spring 10 is wound, it is then heat treated to impart a predetermined range of spring force within a superelastic zone of deflection, as described in U.S. Pat. No. 4,849,032, which is hereby incorporated by reference as part of the present disclosure.

The continuous-length coil spring 10 is then cut into several shorter-length open coil springs 16, shown typically in FIG. 3. The inner diameter "D" of the continuous-length coil spring 10, which is the same as the inner diameter "D" of each coil spring 16, is dimensioned to fit over an archwire (not shown). The free ends of the coil spring 16 are each cut at about the middle of two adjacent closed coil sections 14. Therefore, because each closed coil section 14 includes about three turns, about 1-½ turns on either end of the coil spring 16 are tightly wound substantially without any spacing between the turns thereof.

As a result, each free end of the coil spring 16 defines an engaging surface C, indicated by crosshatch in FIG. 4. Each engaging surface C is equal in length to about one-half of a turn, and is oriented substantially perpendicular to the longitudinal axis X of the coil spring 16. When the coil spring 16 is mounted over an archwire, the engaging surfaces C engage the orthodontic brackets mounted to a patient's teeth (not shown) to impart the compressive force of the coil spring 16 to the brackets.

One advantage of the open coil spring of the present invention, is that because the engaging surfaces C are each equal in length to about ½ of a turn, and are oriented substantially perpendicular to the helical axis X of the spring, the compressive force of the coil spring 16 is accurately imparted to the orthodontic brackets. Known open shape-memory alloy coil springs, on the other hand, are not formed with the closed coil sections, but are typically trimmed at about the midpoints between the turns of the coil springs. Therefore, the free ends of such known coil springs are usually oriented at oblique angles relative to the longitudinal axes of the coil springs, like the angle B shown in FIG. 2. As a result, usually only the tips of the free ends of such springs engage the orthodontic brackets. Accordingly, the force of such a spring is typically inaccurately or unreliably applied to the brackets. Thus, the problems normally encountered with known open shape-memory alloy coil springs, are overcome by forming the continuous-length coil spring 10 with the closed coil sections 14 of the present invention.

As will be recognized by those skilled in the art, the number of turns in each open coil section 12 can be varied, as compared to the embodiment shown in FIG. 2. Likewise, the open coil sections 12 do not have to include the same number of turns, but each can be wound with a different number of turns. Moreover, if needed for an individual patient, a coil spring 16 may comprise two or more open coil sections 12 with a closed coil section 14 formed between each successive open coil section. For example, the length of an open coil section 12 may not be long enough to fit within the space provided between adjacent orthodontic brackets, whereas the length of two or three open coil sections 12 may be appropriate. Therefore, a single spring 16 can be trimmed from a continuous-length coil spring 10 that has more than one open coil section 12 and/or closed coil section 14.

FIG. 5 illustrates another continuous-length coil spring embodying the present invention which is substantially the same as the continuous-length coil spring 10 of FIG. 2. Therefore, like reference numerals are used to indicate like elements. The continuous-length coil spring 10 of FIG. 5 differs from the coil spring described above in that each of the closed coil sections 14 includes about four turns, and each of the open coil sections 12 includes about five turns. Therefore, when the shorter-length open coil springs are cut therefrom, each one has about two turns tightly wound substantially without any spacing on either end thereof. The number of windings in either the open coil sections 12 or closed coil sections 14 can thus be varied to meet the needs of each particular application.

What is claimed is:

1. An open orthodontic coil spring for imparting forces to orthodontic appliances mounted to a patient's teeth, said spring comprising:
    a shape-memory alloy wire exhibiting superelastic properties wound into a coil, said coil defining at least one open coil section between the free ends thereof, said open coil section defining predetermined spaces between the turns thereof, the free ends of said coil being tightly wound substantially without any spacing between the turns thereof, said free ends of said coil thus being adapted to substantially engage orthodontic appliances to impart the forces of said spring thereto for moving a patient's teeth.

2. An open orthodontic coil spring as defined in claim 1, wherein
    said shape-memory alloy wire is made of a nickel-titanium alloy.

3. An open orthodontic coil spring as defined in claim 1, wherein
    said coil spring is heat treated to impart a substantially predetermined range of spring force within a superelastic zone of deflection.

4. An open orthodontic coil spring as defined in claim 1, wherein
    each of said free ends of said coil includes at least 1-½ turns.

5. An orthodontic coil spring as defined in claim 1, wherein
    said coil spring defines an engaging surface on each of said free ends thereof, each of said engaging surfaces being oriented in a plane substantially perpendicular to the longitudinal axis of said coil spring.

6. An orthodontic coil spring as defined in claim 1, wherein
    each of said free ends of said coil defines an engaging surface adapted to substantially engage orthodontic appliances, each of said engaging surfaces being about equal in length to one-half of a turn of said coil.

7. A continuous-length coil spring for cutting several shorter-length open orthodontic coil springs therefrom, said continuous-length coil spring comprising:
    a shape-memory alloy wire exhibiting superelastic properties wound into a coiled shape,
    said coiled shape defining a plurality of open coil sections defining predetermined spaces between the turns thereof and closed coil sections formed between said open coil sections, said closed coil sections being tightly wound with insubstantial spacing between the turns thereof,
    said continuous-length coil spring being separable into more than one shorter-length open orthodontic coil spring by cutting through said shape-memory alloy wire in at least one of said closed coil sections.

8. A continuous-length coil spring as defined in claim 7, wherein
    each of said open coil sections includes the same number of turns and each of said closed coil sections includes the same number of turns.

9. A continuous-length coil spring as defined in claim 8, wherein
    each of said open coil sections includes about five turns and each of said closed coil sections includes about three turns.

10. A continuous-length coil spring as defined in claim 9, wherein
    said shape-memory alloy wire is made of a nickel-titanium alloy.

11. A method of making orthodontic coil springs, said method comprising the following steps:
    winding a shape-memory alloy wire exhibiting superelastic properties into a coil defined by a plurality of open coil sections and closed coil sections located between the open coil sections, the open coil sections being wound to define predetermined spaces between the turns thereof, and the closed coil sections being tightly wound with insubstantial spacing between the turns thereof; and
    cutting through the shape-memory alloy wire in at least one of the closed coil sections to form at least two open orthodontic coil springs therefrom.

12. A method of making orthodontic coil springs as defined in claim 11, wherein
    each of the open coil sections is wound to include the same number of turns and each of the closed coil sections is wound to include the same number of turns.

13. A method of making orthodontic coil springs as defined in claim 12, wherein
    each of the open coil sections is wound to include about five turns and each of the closed coil sections is wound to include about three turns.

14. A method of making orthodontic coil springs as defined in claim 11, wherein
    the coil is cut so that the at least two open orthodontic coil springs formed therefrom each include on either end thereof at least 1-½ tightly wound turns with insubstantial spacing therebetween.

15. A method of making orthodontic coil springs as defined in claim 11, wherein
    the shape-memory alloy wire is a nickel-titanium alloy wire.

16. An open orthodontic coil spring for imparting forces to orthodontic appliances, the coil spring comprising:

a Ni-Ti alloy wire exhibiting superelastic properties wound into a coil, the coil defining closed coil sections on either end thereof and at least one open coil section located between the closed coil sections, wherein each open coil section defines predetermined spaces between the turns thereof, and each closed coil section includes at least 1-½ turns tightly wound substantially without any spacing therebetween, and about ½ of a turn on the end of each closed coil section defines an engaging surface, the engaging surfaces being oriented substantially perpendicular to the longitudinal axis of the coil spring for engaging orthodontic appliances to impart the compressive forces of the open coil spring thereto.

17. A continuous-length orthodontic coil spring comprising:

a Ni-Ti alloy wire exhibiting superelastic properties wound into a coil, the coil having a plurality of open coil sections and closed coil sections located therebetween, the open coil sections defining predetermined spaces between the turns thereof and the closed coil sections each including at least three turns tightly wound substantially without any spacing therebetween, the coil being separable into at least two shorter-length open coil springs by cutting through the Ni-Ti alloy wire in about the middle of at least one of the closed coil sections.

18. A method of making open orthodontic coil springs comprising the following steps:

winding a shape-memory alloy wire exhibiting superelastic properties into a coil having a plurality of closed coil sections and a plurality of open coil sections located between the closed coil sections, the closed coil sections being tightly wound substantially without any spacing between the turns thereof, and the open coil sections being wound defining predetermined spaces between the turns thereof; and cutting through the shape-memory alloy wire in at least one of the closed coil sections to form at least two shorter-length open coil springs therefrom, the free ends of the shorter-length open coil springs being defined by the closed coil sections and thus being adapted to substantially engage orthodontic appliances to impart the forces of the spring thereto.

19. A method of making open orthodontic coil springs as defined in claim 18, wherein the shape-memory alloy wire includes a Ni-Ti alloy and further comprises the following step:

heat treating the coil to impart a substantially predetermined range of spring force within a superelastic zone of deflection.

* * * * *